United States Patent [19]

Mason et al.

[11] Patent Number: 4,725,684

[45] Date of Patent: Feb. 16, 1988

[54] SYNTHESIS OF UREA CYANURATE

[75] Inventors: Robert W. Mason, Lake Charles; Thomas C. Parker, Sulphur, both of La.

[73] Assignee: Olin Corporation, Cheshire, Conn.

[21] Appl. No.: 33,292

[22] Filed: Apr. 2, 1987

[51] Int. Cl.$^4$ ............................................. C07D 251/34
[52] U.S. Cl. ..................................................... 544/223
[58] Field of Search ......................................... 544/223

[56] References Cited

U.S. PATENT DOCUMENTS 3,154,545  8/1964  Symes et al. ........................ 260/248
3,318,887  5/1965  Moore et al. ....................... 260/248
4,018,769  4/1977  Young ................................. 260/248

OTHER PUBLICATIONS

Beilstein, 4. Aufl. Bd. 26., Verlag Von Julius Springer, 1937, pp. 242-243.
Batwa, B. S., Parikh, A. R., (Chem. Abst. 83; 193240y), 1975.
Chemical Abstract, vol. 96, entry 69048w, (1982), Abstract of Japan, Kokai, 81/140979.

Primary Examiner—John M. Ford
Attorney, Agent, or Firm—James B. Haglind; Thomas P. O'Day

[57] ABSTRACT

A process for producing urea cyanurate which comprises reacting an aqueous solution of urea with cyanuric acid at a temperature below the melting point of urea provides reaction conditions which minimize urea decomposition and are energy efficient. The urea cyanurate product can be used directly in the manufacture of cyanuric acid in a process which minimizes the build up of scale on the reactor walls. The cyanuric acid product has reduced concentrations of by-products such as ammelide and ammeline.

10 Claims, No Drawings

SYNTHESIS OF UREA CYANURATE

This invention relates to a process for the production of urea cyanurate.

Urea cyanurate is used as a preservative in the storage of agricultural crops and the production of cyanuric acid.

Previous methods of preparing urea cyanurate from aqueous solutions of urea teach the addition of cyanuric acid to supersaturated aqueous urea at elevated temperatures (Beilstein, 4. Aufl. Bd 26. 242-3). Symes and Vazopolos produced urea cyanurate by the reaction of aqueous urea solutions or molten urea with cyanuric acid at temperatures above 135° C., as described in U.S. Pat. No. 3,154,545, issued Oct. 27, 1964. No yields of urea cyanurate are reported for these processes.

At these elevated temperatures urea is prone to hydrolysis resulting in a loss of yield, and in addition these methods are energy intensive. Further, where the urea cyanurate is used to produce cyanuric acid, the yields of cyanuric acid are generally 70 percent or less and the cyanuric acid contains substantial amounts of impurities such as ammelide.

Now it has been found that urea cyanurate can be produced by the reaction of aqueous solutions of urea with cyanuric acid under conditions which minimize urea hydrolysis and have lower energy requirements.

It is an object of the present invention to provide an improved process for producing urea cyanurate from aqueous urea solutions.

Another object of the invention is to provide a process for producing urea cyanurate under conditions which minimize the undesired hydrolysis of urea.

A further object of the present invention is to provide a process for urea cyanurate having reduced energy requirements.

These and other objects of the invention are accomplished in a process for producing urea cyanurate which comprises reacting an aqueous solution of urea with cyanuric acid at a temperature below the melting point of urea.

More in detail, the novel process of the present invention employs as one reactant an aqueous solution of urea. The solution may contain any suitable concentration of urea. Aqueous solutions of urea used as the reactant include, for example, those having from about 25 percent to about 75 percent by weight, and preferably from about 50 to about 75 percent by weight of urea.

The second reactant is solid cyanuric acid which is available commercially in granular form.

Cyanuric acid and the aqueous urea solution are reacted at temperatures below the melting point of urea to avoid the hydrolysis and decomposition of urea. Temperatures which may be employed include those in the range of from about 40° to about 130° C., and preferably from about 50° to about 90° C.

Amounts of urea and cyanuric acid which may be used in the process of the present invention are not critical. Operation of the process is carried out using an excess of urea, for example, a molar ratio of urea to cyanuric acid in the range of from about 3:1 to 10:1.

Urea cyanurate produced during the reaction precipitates as a solid and is readily recovered by known liquid-solid separations such as filtration, centrifugation, etc.

The urea cyanurate cake recovered in the separation process may be dried by known means to a granular product and sold commercially.

Where the urea cyanurate is to be used in the production of cyanuric acid, the wet cake, containing 3 to 8 percent by weight of water, can be employed directly without further processing.

In an alternate embodiment, the reaction mixture may contain an effective amount of a promoter or catalyst including an ammonium halide such as ammonium chloride or ammonium fluoride.

The pyrolysis of the urea cyanurate cake produces cyanuric acid in a process which minimizes the build up of scale on the reactor walls while providing a product having reduced concentration of by-products such as ammelide and ammeline.

The novel process of the present invention produces urea cyanurate under conditions which minimize urea decomposition and are energy efficient. The urea cyanurate product can be used directly in the manufacture of cyanuric acid.

To further illustrate the process of the invention, the following examples are given without any intention of limiting its scope thereby. All parts, percentages and proportions are by weight unless otherwise indicated.

EXAMPLE 1

A solution of 100 grams of water and 100 grams (1.67 mole) of urea in a reaction vessel was heated to 60° C. with stirring. Cyanuric acid (21.5 g, 0.167 mole) was added and the resulting suspension stirred for 2.0 hours to completely react the cyanuric acid. The product suspension was filtered by vacuum suction. Analysis of an oven dried (14 hours, 110° C.) portion of the recovered solids showed the product to be 45.0 percent urea, 0.7 percent biuret, and 54.3 percent cyanuric acid. The oven dried material was characterized by the infrared spectrum: Nujol mull, 3460, 3320, 1690 (broad), 1600 (broad) cm$^{-1}$.

EXAMPLE 2

An aqueous solution of urea (50 percent, 1200 g) was added to a reaction vessel and heated to 90° C. Cyanuric acid (129 g) and ammonium chloride (12.9 g) were added to the solution and the reaction mixture agitated. During the reaction the temperature was maintained at 90° C. After two hours, the slurry of urea cyanurate was conveyed to a centrifuge and a wet cake of urea cyanurate recovered. The supernatant mother liquor was returned to the reaction vessel and additional urea solution and cyanuric acid added to maintain a mole ratio of urea to cyanuric acid of about 10:1. Additional ammonium chloride (1.0 g) was also added to the reaction mixture. The process was continued for six cycles. After each cycle the urea cyanurate cake was analyzed for moisture the supernatant mother liquor collected and weighed. The wet urea cyanurate cake was dried and the urea and chloride ion concentrations measured. Free urea content of the urea cyanurate cake was estimated from the moisture content of the product cake and dry urea cyanurate content then back calculated. The results are given in Table I below:

TABLE I

| | UREA CYANURATE SYNTHESIS | | | | |
|---|---|---|---|---|---|
| Cycle | Urea (g) | Water (g) | CA* (g) | NH$_4$Cl (g) | Supernatant ML** (g) |
| 1 | 600.0 | 600 | 129 | 12.9 | — |

TABLE I-continued

| Cycle | | | | | |
|---|---|---|---|---|---|
| 2 | 45.7 | — | 129 | 1.0 | 1193.12 |
| 3 | 54.0 | — | 129 | 1.0 | 1176.67 |
| 4 | 60.0 | — | 129 | 1.0 | 1176.67 |
| 5 | 60.0 | — | 129 | 1.0 | 1141.36 |
| 6 | 60.0 | — | 129 | 1.0 | 1131.86 |

UREA CYANURATE PRODUCT

| Cycle | Wet U CA*** (g) | Moisture (%) | Free Urea (g) | Dry U CA (g) | % Urea | % Cl |
|---|---|---|---|---|---|---|
| 1 | 143.39 | 3.5 | 5.02 | 133.35 | 34.35 | 0.12 |
| 2 | 180.56 | 4.8 | 8.67 | 163.22 | 34.00 | 0.13 |
| 3 | 187.56 | 6.1 | 11.44 | 164.68 | 33.49 | 0.18 |
| 4 | 183.92 | 4.9 | 9.01 | 165.90 | 33.11 | 0.12 |
| 5 | 182.40 | 4.9 | 8.93 | 165.54 | 33.36 | 0.15 |
| 6 | 186.02 | 7.8 | 14.54 | 156.94 | 34.84 | 0.22 |

*CA = cyanuric acid
**ML = mother liquor
***U CA = urea cyanurate

EXAMPLE 3

Using the procedure of Example 2, an aqueous solution of urea and granular cyanuric acid were reacted at 90° C. to produce urea cyanurate. Portions of the product were removed from the reaction mixture at selected times and the composition analyzed for the concentrations of urea, cyanuric acid, and moisture. Results are given in Table II below.

TABLE II

| Time | Urea (%) in Supernatant Mother Liquor | Urea Cyanurate Product | | |
|---|---|---|---|---|
| | | Urea % | CA* % | Moisture % |
| (1) 0 hr | 62.75 | — | — | — |
| (2) 0.5 hr | 60.50 | 30.57 | 64.23 | 5.19 |
| (3) 1.0 hr | 60.50 | 32.02 | 63.37 | 4.61 |
| (4) 1.5 hrs | 60.25 | 31.22 | 64.49 | 4.29 |
| (5) 2.0 hrs | 60.25 | 33.85 | 61.62 | 4.52 |

*CA = cyanuric Acid

What is claimed is:

1. A process for producing urea cyanurate which comprises reacting an aqueous solution of urea with cyanuric acid at a temperature below the melting point of urea.
2. The process of claim 1 in which the aqueous solution of urea contains from about 25 percent to about 75 percent by weight of urea.
3. The process of claim 1 in which the reaction temperature is from about 40° C. to about 130° C.
4. The process of claim 1 in which an excess amount of urea is present.
5. The process of claim 1 in which an effective amount of an ammonium halide is present.
6. The process of claim 2 in which the aqueous solution contains from about 50 to about 75 percent by weight of urea.
7. The process of claim 5 in which the ammonium halide is ammonium chloride or ammonium fluoride.
8. The process of claim 7 in which the molar ratio of urea to cyanuric acid is from about 3:1 to about 10:1.
9. The process of claim 8 in which the reaction temperature is from about 50° C. to about 90° C.
10. The process of claim 9 in which the ammonium halide is ammonium chloride.

* * * * *